US00PP37056P3

(12) United States Plant Patent
Deng

(10) Patent No.: US PP37,056 P3
(45) Date of Patent: Oct. 21, 2025

(54) ***CALADIUM* PLANT NAMED 'UF-R301'**

(50) Latin Name: *Caladium x hortulanum*
Varietal Denomination: UF-R301

(71) Applicant: Florida Foundation Seed Producers, Inc., Marianna, FL (US)

(72) Inventor: Zhanao Deng, Riverview, FL (US)

(73) Assignee: Florida Foundation Seed, Producers, Inc., Marianna, FL (US)

( * ) Notice: Subject to any disclaimer, the term of this patent is extended or adjusted under 35 U.S.C. 154(b) by 0 days.

(21) Appl. No.: 19/032,725

(22) Filed: Jan. 21, 2025

(65) Prior Publication Data

US 2025/0241216 P1 Jul. 24, 2025

Related U.S. Application Data

(60) Provisional application No. 63/623,981, filed on Jan. 23, 2024.

(51) Int. Cl.
*A01H 5/12* (2018.01)
*A01H 6/00* (2018.01)

(52) U.S. Cl.
USPC ..... Plt./373
CPC ..... *A01H 6/00* (2018.05); *A01H 5/12* (2013.01)

(58) Field of Classification Search
USPC ..... Plt./373
CPC ..... A01H 5/12; A01H 5/00; A01H 6/10
See application file for complete search history.

(56) References Cited

PUBLICATIONS

Blue Buddha Farm retrieved on Apr. 2, 2025 at https://bluebuddhafarm.com/products/limelite-caladium-bulbs-2-bulbs-preorder-for-spring-2025-stunning-lime-green-leaves-with-blush-pink-speckles?srsltid=AfmBOoonDxRtHbY6ClkXJe92XUmdVH8wWbJJ64Eailp534mUMR6hu-dK, 3pp. (Year: 2025).*

* cited by examiner

*Primary Examiner* — June Hwu
(74) *Attorney, Agent, or Firm* — James R. Holm

(57) ABSTRACT

A new and distinct cultivar of *Caladium* plant named 'UF-R301', characterized by its compact, moderately vigorous growth habit; heart-shaped, peltate leaves that have a yellow, yellow-green, green-yellow, or green-white background color, numerous light red-purple spots, a red-purple basal notch, and midrib and primary veins that are red-purple near the center of leaf and gradually change into white or green-white near the leaf margin; and good to excellent tolerance to sunburns, and high tuber yield potential.

3 Drawing Sheets

CROSS-REFERENCE TO RELATED APPLICATIONS

This Application is related to and claims the benefit of U.S. Provisional Patent Application Ser. No. 63/623,981 filed on Jan. 23, 2024, entitled *CALADIUM* CULTIVARS, the entirety of which is incorporated herein by reference.

Genus and species: *Caladium* x *hortulanum.*

Cultivar denomination: 'UF-R301'.

BACKGROUND OF THE NEW CULTIVAR

The present invention relates to a new and distinct cultivar of *Caladium*, botanically known as *Caladium* x *hortulanum*, and hereinafter referred to by the name 'UF-R301'. *Caladium* plants are tuberous-rooted plants and typically have attractive heart-shaped or arrow-shaped leaves on long stalks rising directly from the tubers. Foliage may grow in a variety of colors and variegation patterns, and many species have been developed for aesthetic coloration, good container and landscape growth, drought tolerance, pest resistance, and other desirable characteristics.

Plant Breeder's Rights for this cultivar have not been applied for. Applicant asserts that no publications or advertisements relating to sales, offers for sale, or public distribution occurred more than one year prior to the effective filing date of this application. Any information about the claimed plant would have been obtained from a direct or indirect disclosure from the Inventor. Applicant claims a prior art exemption under 35 U.S.C. 102(b)(1) for disclosures and/or sales that fall within a one-year grace period prior to the effective filing date of this application.

SUMMARY OF THE INVENTION

The new *Caladium* cultivar 'UF-R301' has not been observed under all possible environmental conditions. The phenotype of the new cultivar may vary with variations in environment and cultural practices such as temperature, light intensity, fertilization, irrigation, and application of plant growth regulators without any change in genotype.

The objective of the breeding program that produced the present cultivar was to develop cultivars that have novel foliar characteristics, produce multiple brightly colored leaves, have good tuber yield potential, and perform well in containers and the landscape. The present *Caladium* cultivar originated from a cross-pollination made in 2001 in Bradenton, Florida between the *Caladium* x *hortulanum* cultivar 'Miss Muffet' (unpatented), as the female or seed parent, and the *Caladium* x *hortulanum* cultivar 'Gingerland' (unpatented), as the male or pollen parent. The new *Caladium* cultivar was discovered and selected by the inventor as a single plant within the progeny of the stated cross-pollination in Bradenton, Florida in 2005.

Asexual reproduction of the new cultivar 'UF-R301' by tuber divisions in a controlled environment has been performed annually in Bradenton and Wimauma, Florida since 2006. The unique features of this new *Caladium* cultivar are stable and reproduced true to type in successive generations of asexual reproduction.

The new cultivar 'UF-R301' has not been observed under all possible environmental conditions. The phenotype may vary somewhat with variations in environment such as temperature and light intensity, without, however, any variance in genotype.

The following traits have been repeatedly observed and are determined to be the unique characteristics of 'UF-R301'. These characteristics in combination distinguish 'UF-R301' as a new and distinct cultivar of *Caladium:*

1. Compact growth habit;
2. Heart-shaped, peltate leaves with a yellow, yellow-green, green-yellow, or green-white background color, numerous light red-purple leaf spots, and a midrib and primary veins that are red-purple near the center of the leaf and gradually change into yellow, yellow-green, green-yellow, or green-white near the leaf margin;
3. Strong tolerance to sunburn; and
4. High tuber yield.

Plant of the new *Caladium* cultivar 'UF-R301' differ from plants of the female parent and commercial *Caladium* cultivar, 'Miss Muffet', in the following characteristics:

1. Plants of 'UF-R301' are taller than plants of Miss Muffet, whereas 'Miss Muffet' is shorter and more compact and has more leaves than 'UF-R301';
2. Leaves of 'UF-R301' are larger than leaves of 'Miss Muffet'; and
3. Leaves of 'UF-R301' have a uniform yellow-green background color and have light red-purple spots, thus providing a light pink tone, whereas leaves of 'Miss Muffet' have dark red spots and an overall red tone.

Plants of the new *Caladium* cultivar 'UF-R301' differ from plants of the male parent and commercial *Caladium* cultivar, 'Gingerland', in the following characteristics:

1. Plants of 'UF-R301' are more densely foliated than plants of 'Gingerland';
2. Leaves of 'UF-R301' are of the fancy type and are peltate and heart-shaped with light to no undulation, whereas leaves of 'Gingerland' are of the lance or strap type and are much more elongated than leaves of 'UF-R301';
3. Leaves of 'UF-R301' have light red-purple spots, whereas leaves 'Gingerland' have brick-red spots; and
4. Petioles of 'UF-R301' are lighter in color than the petioles of 'Gingerland'.

DESCRIPTION OF THE FIGURES

The accompanying photographs (as shown in FIGS. 1-3) illustrate the overall appearance of the new *Caladium* cultivar 'UF-R301'. These photographs show the colors as true as can be reasonably obtained in colored reproductions of this type. Colors in the photographs may differ slightly from the color values cited in the detailed botanical description, which accurately describes the colors of the new *Caladium* cultivar.

DETAILED BOTANICAL DESCRIPTION OF THE CULTIVAR

Figure 1:
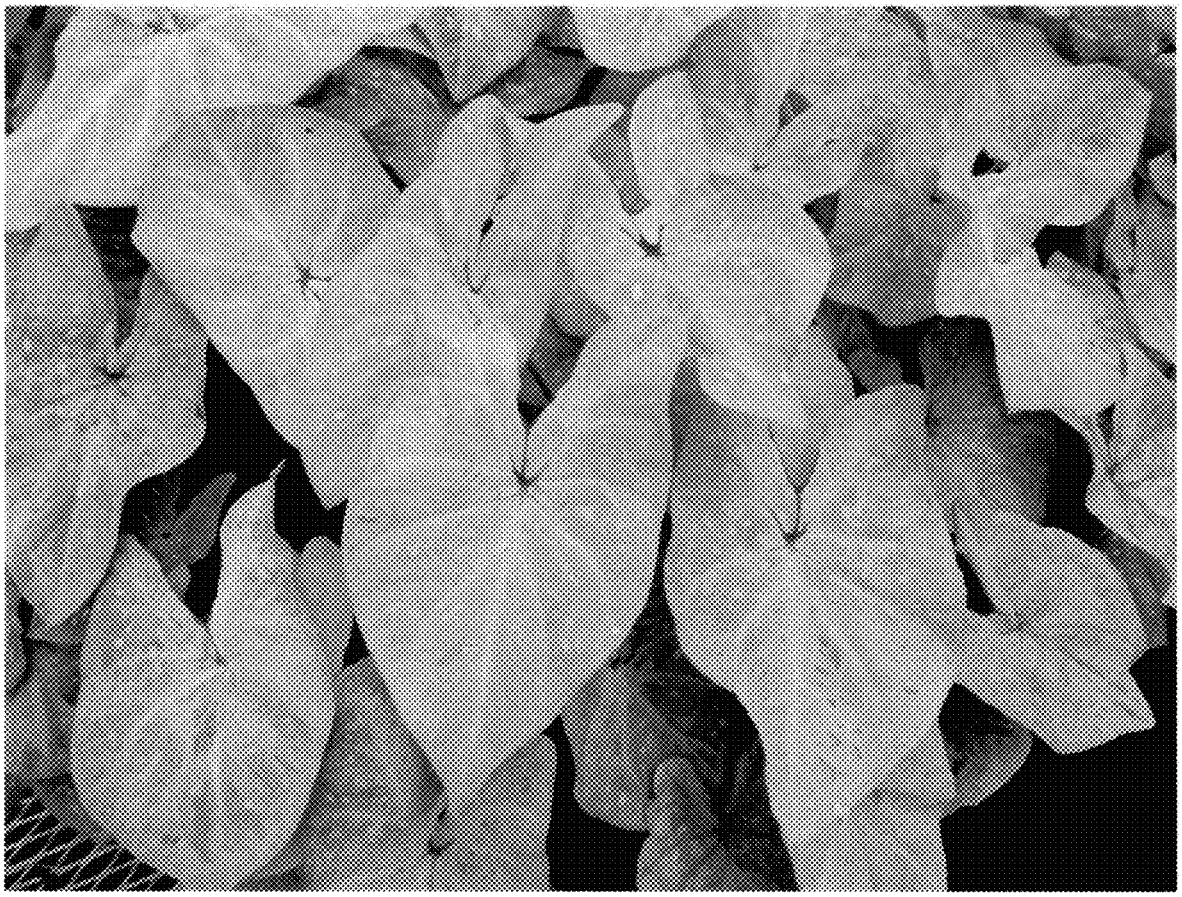
FIG. 1 shows a side perspective view of a typical plant of 'UF-R301' grown in a container in a greenhouse.
Figure 2:
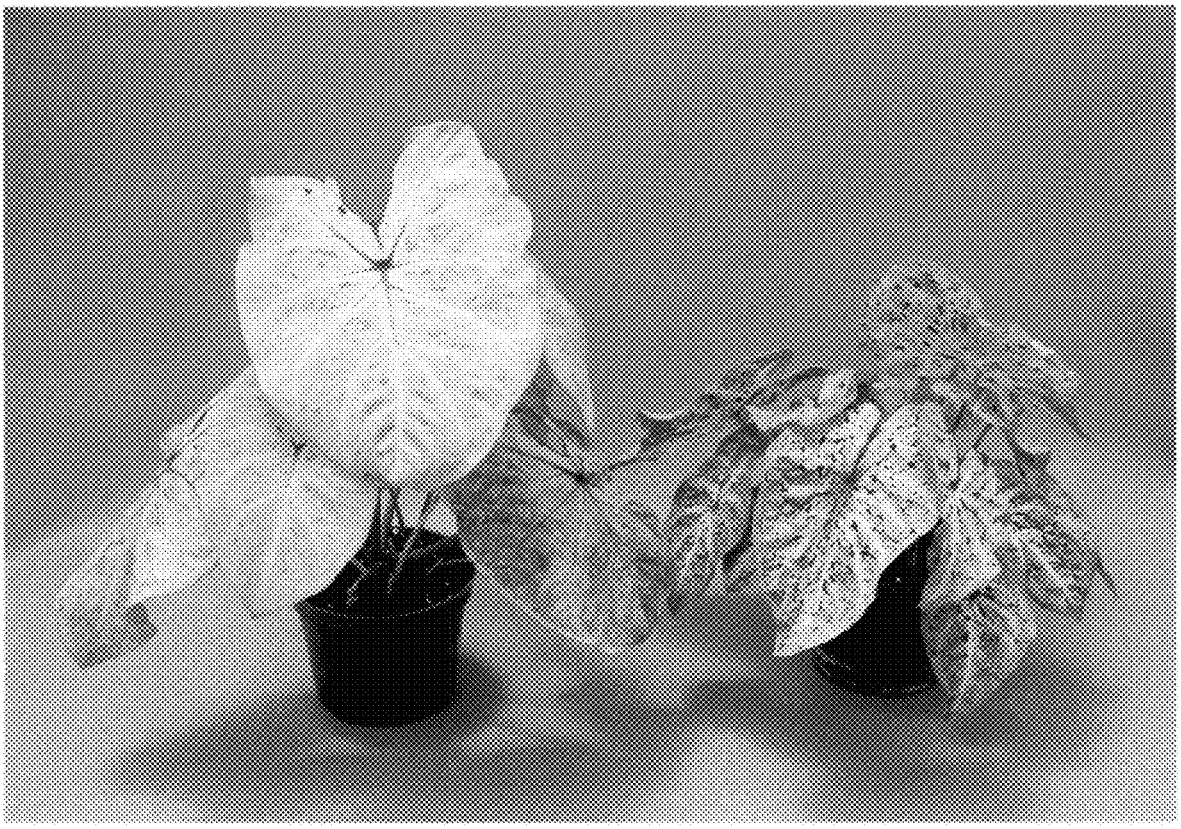
FIG. 2 shows a side perspective view of typical plants of 'UF-R301' (left) and the seed parent 'Miss Muffet' grown in a greenhouse, both plants were forced from one No. 1-sized intact tuber and grown in containers inside a shaded greenhouse.
Figure 3:
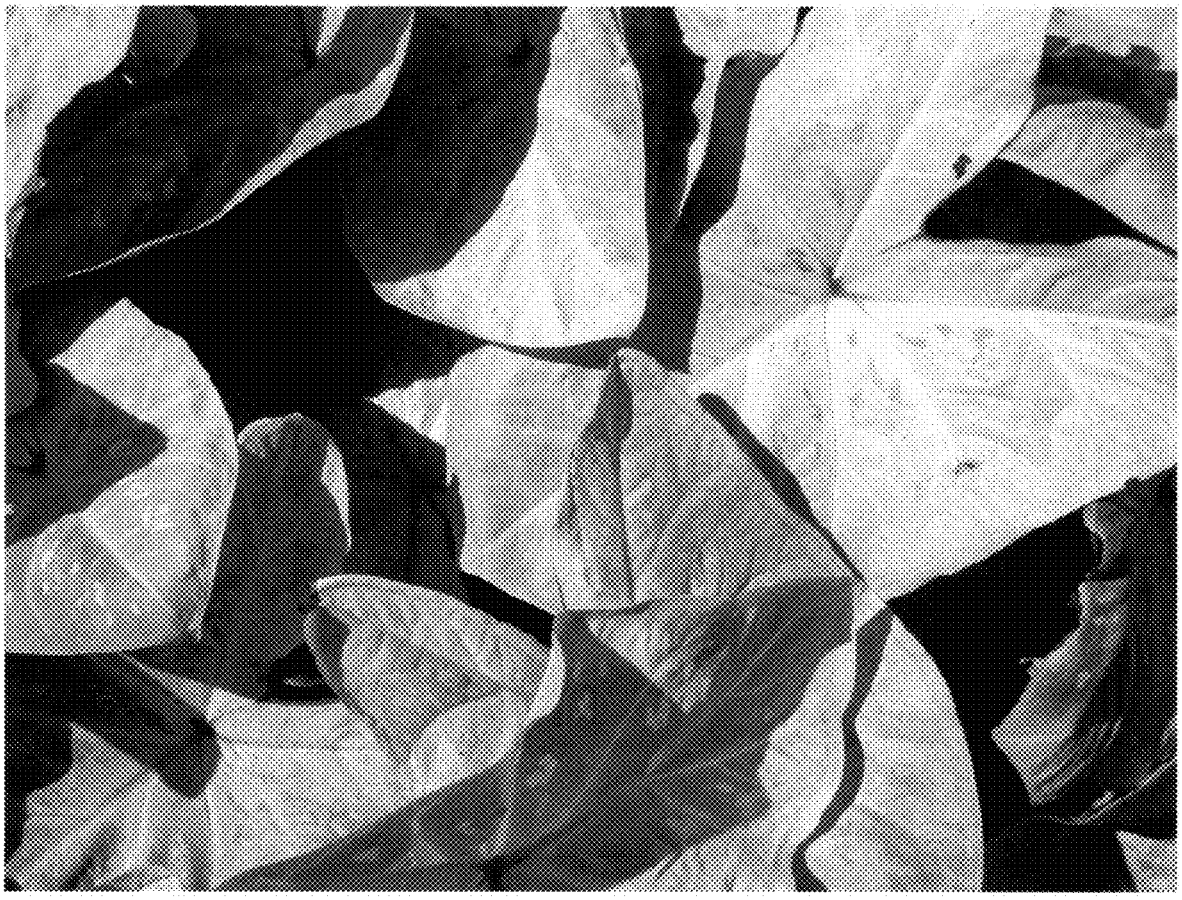
FIG. 3 shows a top view of typical plants of 'UF-R301' grown in an outdoor nursery in full sun.

In the following description, color references are made to The Royal Horticultural Society (R.H.S.) Colour Chart, 1986 Edition, except where general terms of ordinary dictionary significance are used.

Description of Growing Conditions

The aforementioned photographs and the following observations and measurements describe plants grown in 15-cm containers in Wimauma, Florida during the summer in a polypropylene-covered shade house and also describe plants grown in an outdoor nursery in ground beds in Wimauma, Florida during the late summer. All plants were grown under conditions and practices that approximate those generally used in commercial *Caladium* production.

During the production of the plants, day temperatures ranged from about 26° C. to 35° C., night temperatures ranged from about 18° C. to 26° C. and light levels ranged from 2400 to 3840 foot-candles in the greenhouse to 8300 foot-candles for plants grown in the outdoor nursery. Plants grown in the greenhouse were 3 months old from tubers when the photographs and the detailed description were taken. Plants grown in the outdoor nursery were about 4 months old from tubers when the photographs and the detailed description were taken.

Botanical Description

Botanical classification:

*Family.*—Araceae.

*Botanical name: Caladium* x *hortulanum.*

*Common name.—Caladium* or *Caladium.*

*Cultivar.*—'UF-R301'.

Parentage:

*Female or seed parent.—Caladium* x *hortulanum* cultivar 'Miss Muffet' (unpatented).

*Male or pollen parent.—Caladium* x *hortulanum* cultivar 'Gingerland' (unpatented).

Propagation:

*Type.*—By tubers and by tuber divisions.

*Time to initiate roots, summer.*—About seven to ten days at 32° C.

*Time to initiate roots, winter.*—About two to three weeks at 24° C.

Tuber description:

*Number of buds per tuber (greenhouse-grown plants).*—About 4 to 6 actively growing buds/shoots.

*Number of buds per tuber (outdoor nursery-grown plants).*—About 4 to 6 actively growing buds/shoots.

*Height.*—4.0 cm.

*Diameter.*—3.7 cm.

*Texture.*—Thick, starchy, and hairy with fine dried roots.

*Color*.—Epidermis: 27A (orange) to 164A and 177A (greyed-orange). Interior: 14B (yellow-orange).

Root description: Dense, thick, and white fleshy roots.

Plant description:

*Type*.—Herbaceous perennial.

*Growth habit*.—Moderately vigorous, dense growth habit with an abundance of leaves, suitable for growing in 10 to 25-cm sized containers.

*Leaf petioles*.—Arising from tubers, mostly upright, curving outwardly with development.

*Plant height, from soil level to top of leaf plane*.—Greenhouse grown plants: Average 35.6 cm. Outdoor nursery grown plants: Average 50.0 cm.

*Plant height, from soil level to top of the inflorescences*.—Greenhouse grown plants: Average 26.4. Outdoor nursery grown plants: Average 30.0 cm.

*Plant diameter or spread*.—Greenhouse-grown plants: Average 68.1 cm. Outdoor nursery grown plants: Average 55.7 cm.

Foliage description:

*Length*.—Greenhouse grown plants: Average 27.0 cm. Outdoor nursery grown plants: Average 28.4 cm.

*Width (flattened)*.—Greenhouse grown plants: Average 18.3 cm. Outdoor nursery grown plants: Average cm 19.4 cm.

*Shape*.—Ovate to cordate.

*Apex*.—Acuminate.

*Base*.—Peltate and cordate.

*Margin*.—Entire.

*Texture*.—Upper surface: Smooth, glabrous. Lower surface: Smooth, glabrous; glaucous.

*Venation pattern*.—Pinnate.

*Color, developing leaves (greenhouse grown plants)*.—Upper surface: Interveinal areas: 8C (yellow) flanking the primary vein and secondary veins than becoming 157B (green-white) slightly within the interveinal areas; 144A (yellow-green) and 138A (green) centered within the interveinal areas and towards and along the leaf margin; an average of 56 spots of 155C (white) and 62B and 64C (light red-purple) across the leaf surface; spots measure up to 2 cm in length and up to 0.6 cm in width. Borders and margins: 137C and 143A (green) with a thin line of 58A and 64A (red-purple) on the extreme edge between the upper and lower leaf surface. Basal notch: 58A, 62C and 64A (red-purple). Venation: Mid rib: 58A (red-purple) in the proximal area and 142B (green) to 146A (yellow-green) in the distal area. Primary veins: 143A (green) to 146A (yellow-green) with streaks in the proximal area of 58A (red-purple). Lower surface: Interveinal areas: 191A (greyed-green) to 139C (green) with an average of 55 spots of 62C (red-purple) to 159B (orange-white), spots measuring up to 1.1 cm in length and up to 0.6 cm in width. Border and margins: 191A (greyed-green) to 138B (green). Venation: Midrib: 58A (red-purple) in the proximal area and 137D and 138C (green) in the distal area. Primary veins: 58A (red-purple) in the proximal area and 138C (green) in the distal area.

*Color, fully expanded leaves (greenhouse grown plants)*.—Upper surface: Interveinal areas: 8C (yellow) flanking the primary vein and secondary veins than becoming 149D (yellow green) within the interveinal areas, shaded leaves will develop some darker interveinal areas of 143C and 143D (green); an average of 119 spots of 155B (white) and 62B (red-purple) across the leaf surface; spots measure up to 1.5 cm in length and up to 0.8 cm in width. Borders and margins: 143C (green) with a thin line of 60A to 60B (red-purple) on the extreme edge between the upper and lower leaf surfaces. Basal notch: 60A (red-purple). Venation: Mid rib: 60A to 71D (red-purple) in the proximal area and 138D (green) and 144D (yellow-green) in the distal area. Primary veins: 60A (red-purple) in the proximal area and 144C (yellow-green) or 138B (green) in the distal area. Lower surface: Interveinal areas: 138B to 138C (green) and 147C (yellow-green) with an average of 89 spots of 62D and 73C (red-purple), spots measuring up to 1.7 cm in length and up to 0.8 cm in width. Border and margins: 138B (green) or 147C (yellow-green). Venation: Mid rib: 146C and 147C (yellow-green). Primary veins: 147D (yellow-green) to 195D (greyed-green).

*Color, developing leaves (outdoor nursery grown plants)*.—Upper surface: Interveinal areas: Mostly 145D (yellow-green) with some 8C (yellow) flanking the primary vein and secondary veins; an average of 62 spots of 155D (white) and 61D (red-purple) across the leaf surface; spots measure up to 0.9 cm in length and up to 0.3 cm in width. Border and margins: 141A (green) and 146B (yellow-green) towards the border with a very thin line of 60A (red-purple) between the upper and lower leaf surfaces. Venation: Midrib: 60A (red-purple) in the proximal area and 146C (yellow-green) in the distal area. Primary veins: 60C (red-purple) in the proximal area and 146C (yellow-green) in the distal area with netted veins of 146D (yellow-green). Lower surface: Interveinal areas: 138B and 139C (green) with an average of 52 spots of 35C (orange-red), spots measure up to 0.4 cm in length and up to 0.3 cm in width. Border and margins: 139C (green). Venation: Midrib: 8D (yellow) and 20D (yellow-orange). Primary veins: 148C (yellow-green).

*Color, fully expanded leaves (outdoor nursery grown plants)*.—Upper surface: Interveinal areas: 147D (yellow-green) with some 8C (yellow) flanking the primary vein and secondary veins, shaded leaves will develop some darker interveinal areas of 143B (yellow-green); an average of 76 spots of 155D (white) and 59D (red-purple) across the leaf surface; spots measure up to 1.5 cm in length and up to 0.3 cm in width. Border and margins: 146D (yellow-green). Venation: Midrib: 147D (yellow-green) to 139D (green) with streaks of 59C (red-purple). Primary veins: 185A (greyed-purple) in the proximal area and 148C in the distal area. Lower surface: Interveinal areas: 146B (yellow-green) with an average of 44 spots of red-62D (purple), spots measuring up to 1.1 cm in length and up to 0.4 cm in width. Border and margins: 146B (yellow-green). Venation: Midrib: 26D (orange). Primary veins: 148C to 148D (yellow-green).

*Petiole*.—Aspect: Mostly erect, curving outwardly with development. Length: Greenhouse grown plants: Average 38.4 cm. Outdoor nursery grown plants: Average 45.9 cm. Diameter, distal: Greenhouse grown plants: Average 4.5 mm. Outdoor nursery grown plants: Average 4.7 mm. Greenhouse grown plants: Average 7.3 mm. Outdoor nursery grown plants: Average 7.5 mm. Strength: Strong and flexible. Color: Diameter, proximal: Greenhouse grown plants: 179B (greyed-red) or 36C (red) and variably streaked with 200A (brown) and 202A (black). Outdoor nursery grown plants: 182A (greyed-red) with streaks of 182A (greyed-red) or 187A (greyed-purple). Wing length: Greenhouse grown plants: Average 7.7 cm. Outdoor nursery grown plants: Average 4.2 cm. Wing diameter: Greenhouse grown plants: Average 9.2 mm. Outdoor nursery grown plants: Average 4.5 mm. Wing color: Greenhouse grown plants: 31C (orange-red) with streaks of 200A (brown). Outdoor nursery grown plants: 160D (greyed-yellow), 164D (greyed-orange), or 27B (orange) with streaks of 187A (greyed-purple).

Inflorescence description: Only observed on greenhouse-grown plants.

*Arrangement*.—Upright hooded spathes surrounding a columnar spadix borne on a tall upright scape. Spadix with sessile, simple female and male flowers separated into two zones: female flowers arranged on the lower one-third of the spadix, male flowers arranged on the upper two-thirds of the spadix. Sterile flowers develop between female and male flower zones; near this area, the spathe constricts surrounding the female flowers.

*Fragrance*.—None detected.

*Natural flowering season*.—'UF-R301' typically flowers during the spring or early summer in central Florida; flowers develop about seven weeks after growth commences and inflorescences last about three days before fading, inflorescences are persistent.

*Spathe*.—Length: Average 7.9 cm. Width, distal: 2.8 cm. Width, proximal: 2.4 cm. Shape: Ovate to somewhat obovate. Apex: Acute to acuminate. Base: Tapering. Margin: Entire. Texture, upper and lower surfaces: Smooth, glabrous. Color: Front surface: Upper two-thirds: 155B (white). Lower one-third: 137B (green). Rear surface: Upper two-thirds: 158D (yellow-white) and 137C (green). Lower one third: 137C (green).

*Spadix*.—Length, entire spadix: Average 5.3 cm. Shape: Spindle-shaped to columnar. Apex: Obtuse. Base: Obtuse. Aspect: Upright. Male flower zone: Length: Average 2.9 cm. Diameter: Average 8.2 mm. Color, mature: 159C (orange-white). Male flowers: Quantity per spadix: Average 150. Shape: Obovate. Height: Average 2.3 mm. Diameter: Average 2.3 mm. Anthers: Non observed. Pollen: Non observed. Sterile flower zone: Length: Average 0.7 cm. Diameter: Average 6.8 mm. Color, mature: 159D (orange-white). Female flower zone: Length: Average 1.7 cm. Diameter: Average 9.2 mm. Color: 161D (greyed-yellow). Female flowers: Quantity per spadix: Average 140. Shape: Obovate. Height: Average 2.7 mm. Diameter: Average 1.9 mm. Ovary color: 19D (yellow-orange).

*Scape*.—Length: Average 18.4 cm. Diameter: Average 7.5 mm. Strength: Sturdy and flexible. Aspect: Erect. Texture: Smooth, glabrous; glaucous. Color: Lower one-third: 62D (red-purple). Middle one-third: Close to 27A (orange). Upper one-third: Close to 137C (green). Just below the spathe: 137C (green).

*Seeds and fruit*.—Seed and fruit development have not been observed.

Disease and pest resistance: Disease and pest resistance have not been observed on plants of 'UF-R301' grown in the field or in the greenhouse.

Sunburn resistance: Plants of the new *Caladium* 'UF-R301' have been observed to be tolerant to sunburn in open outdoor nurseries or fields.

Temperature tolerance: Plants of the new *Caladium* 'UF-R301' have been observed to be tolerant to temperatures up to about 40° C.

Tuber Yield Potential

The new *Caladium* 'UF-R301' was also evaluated for tuber production and plant performance at the Wimauma, Florida in 2014 and compared to plants of the commercial *Caladium* cultivar 'Miss Muffet'. The soil was an EauGallie fine sand with approximately 1% organic matter and a pH of 6.2. *Caladium* plants were grown in the open field using a plastic mulched, raised bed system. Field plots were organized in a randomized complete block design consisting of three replications. Each plot was 1.2 $m^2$ and contained 30 *Caladium* propagules. Field beds were fumigated on January 9 with Pic-Clor 60 (39.0% 1,3-dichloropropene, 59.6% chloropicrin) at 448 $kg \cdot ha^{-1}$. Plantacote® Pluss, a controlled-release fertilizer (14N-3.9P-12.5K) was incorporated into the bed at 336 $kg \cdot ha^{-1}$. *Caladium* seed pieces were planted on April 28 at approximately 15-cm spacing between rows and in rows. Irrigation was by seepage to maintain a relatively consistent water table below the covered beds. *Caladium* plants were fertilized with 600 ppm of nitrogen with a commercial water-soluble fertilizer (20N-8.7P-16.6K) on September 18 and Oct. 1, 2014. New crop tubers were dug and washed on December 7 and 8 and air-dried for approximately 60 days inside a greenhouse. Dried tubers were weighed, graded, and counted on Feb. 10, 2015. Tuber grading was by the maximum diameter: Mammoth (8.9 to 11.4 cm), Jumbo (6.4 to 8.9 cm), No.1 (3.8 to 6.4 cm), and No. 2 (2.5 to 3.8 cm). Tuber grades and counts were converted into a production index to show the relative economic value of the harvested tubers per field plot: Production index=6n (Mammoth)+4n (Jumbo)+2n (No.1)+1n (No.2), where n=number of tubers in the grade. The relative values assigned to the five tuber grades in calculating production index were based on the relative market prices provided by Florida *Caladium* tuber producers.

'UF-R301' produced significantly more marketable tubers (41.3 vs. 33.7) and had a greater production index (130 vs. 96) than 'Miss Muffet' in 2014 (Table 1).

TABLE 1

| | Tuber | | |
|---|---|---|---|
| Cultivar | Weight (kg) | Marketable (no.) | Production index |
| 'UF-R301' | 3.66 | 41.3 a | 130 a |
| 'Miss Muffet' | 3.33 | 33.7 b | 96 b |

TABLE 1-continued

| P value | .3663 | .0075 | .0315 | .0470 | .2533 | .8024 | .5544 |
|---|---|---|---|---|---|---|---|

| | Tuber grade distribution (%) | | | |
|---|---|---|---|---|
| Cultivar | Mammoth | Jumbo | No. 1 | No. 2 |
| 'UF-R301' | 13.6 a | 33.1 | 39.7 | 13.5 |
| 'Miss Muffet' | 2.8 b | 43.6 | 38.6 | 15.1 |

Tuber weight, marketable number, production index, and grade distribution of 'UF-R301' and the commercial caladium cultivar 'Miss Muffet' in replicated experimental field plots in Wimauma, Florida. Values presented are means of three plots with 30 propagules planted in a plot of 1.2 $m^2$.

I claim:

1. A new and distinct cultivar of *Caladium* plant named 'UF-R301' as illustrated and described herein.

* * * * *